(12) United States Patent
Keydar et al.

(10) Patent No.: US 9,347,874 B2
(45) Date of Patent: May 24, 2016

(54) CALCULATING THE SPECTRAL CHARACTERISTICS OF THE COLOR RESULTING FROM OVERLAYING COLORANTS

(71) Applicant: Esko Software BVBA, Ghent (BE)

(72) Inventors: Moshe Keydar, Holon (IL); Baldewin Meireson, Ghent (BE)

(73) Assignee: Esko Software BVBA, Ghent (BE)

( * ) Notice: Subject to any disclaimer, the term of this patent is extended or adjusted under 35 U.S.C. 154(b) by 631 days.

(21) Appl. No.: 13/870,940

(22) Filed: Apr. 25, 2013

(65) Prior Publication Data
US 2013/0289941 A1   Oct. 31, 2013

Related U.S. Application Data

(60) Provisional application No. 61/639,718, filed on Apr. 27, 2012.

(51) Int. Cl.
| | |
|---|---|
| *H03F 1/26* | (2006.01) |
| *G01J 3/46* | (2006.01) |
| *G01N 21/25* | (2006.01) |
| *G06K 15/02* | (2006.01) |
| *H04N 1/60* | (2006.01) |
| *H04N 1/54* | (2006.01) |

(52) U.S. Cl.
CPC ............... *G01N 21/255* (2013.01); *H04N 1/54* (2013.01); *H04N 1/6097* (2013.01)

(58) Field of Classification Search
CPC ..... G01N 21/255; G01N 33/32; H04N 1/6097; H04N 1/54; H04N 1/6033; G01J 3/46; G01J 3/462; G01J 3/463; G01J 3/52
USPC ............ 702/127, 189; 356/402, 408; 358/1.2, 358/1.9
See application file for complete search history.

(56) References Cited

U.S. PATENT DOCUMENTS

| | | | |
|---|---|---|---|
| 5,612,902 A | 3/1997 | Stokes | |
| 5,731,989 A | 3/1998 | Tenny et al. | ................... 358/1.9 |
| 5,790,186 A | 8/1998 | Tenny et al. | ................... 348/88 |
| 5,864,834 A | 1/1999 | Arai | |
| 5,933,578 A | 8/1999 | Van de Capelle et al. | |

(Continued)

OTHER PUBLICATIONS

"Predictability of Spot Color Overprints", Chung et al, 35th Int'l Research Conference, Sep. 7-10, 2008, Valencia, Spain.

(Continued)

*Primary Examiner* — An Do
(74) *Attorney, Agent, or Firm* — Dov Rosenfeld; Inventek

(57) ABSTRACT

A method of spectrally characterising an ink printed over another ink, and of calculating a spectral measure of reflectance of an overprint of a plurality of inks thus characterized. The method uses spectral measurements of a substrate. For an order of printing an overprint, for each ink, for a respective amount of printing of the ink, the method accepts or determines a respective interaction of absorption and reflection function ("IAR function") indicative of how the ink interacts with a printed background and includes determining the spectral reflectance by repeatedly multiplying, in the order, for each additional ink added to a current background the spectral measure of the current background by exponentiation of the ratio of the spectral measure of the additional ink on the substrate to the spectral measure of the substrate, by the TAR function of the additional ink.

22 Claims, 13 Drawing Sheets

(56) References Cited

U.S. PATENT DOCUMENTS

| | | | |
|---|---|---|---|
| 6,108,442 | A | 8/2000 | Edge et al. |
| 6,483,607 | B1 | 11/2002 | Van de Capelle et al. |
| 6,646,763 | B1 | 11/2003 | Estrada .................... 358/1.9 |
| 6,671,067 | B1 | 12/2003 | Adam et al. |
| 7,016,042 | B2 | 3/2006 | Edge et al. |
| 7,123,380 | B2 | 10/2006 | Van de Capelle |
| 7,199,903 | B2 | 4/2007 | Van de Capelle et al. |
| 7,397,582 | B2 | 7/2008 | Tin |
| 7,417,769 | B2 | 8/2008 | Hasler et al. |
| 7,433,102 | B2 * | 10/2008 | Takahashi ............ H04N 1/6033 345/600 |
| 7,580,150 | B2 | 8/2009 | Mahy et al. |
| 7,738,142 | B2 | 6/2010 | Edge |
| 7,738,148 | B2 | 6/2010 | Edge |
| 7,773,256 | B2 | 8/2010 | Edge |
| 7,940,393 | B2 | 5/2011 | Noy et al. .................... 356/408 |
| 9,224,080 | B2 * | 12/2015 | Kubota ............... G01N 21/278 |
| 2008/0273202 | A1 | 11/2008 | Noy et al. .................... 356/408 |

OTHER PUBLICATIONS

"Predicting Pictorial Color Image Match", Chung et al, retrieved Feb. 21, 2012 from http://cias.rit.edu/~gravure/bob/pdf/2008_TAGA_PCRI.pdf.

"Spectral reflectance estimation from multi-band image using color chart", Murakami et al, Optics Communications 188 (2001) 47-54, Feb. 1, 2001.

"An Investigation of Multispectral Imaging for the Mapping of Pigments in Paintings", Zhao et al, Proc. SPIE 6810, Computer Image Analysis in the Study of Art, Feb. 29, 2008.

"Predicting Color of Overprint Solid", Chung et al, Proceedings of the 36th IARIGAI Research Conference, Advances in Color Reproduction, Stockholm, Sweden, 2009.

"Estimating Spectral Reflectances of Digital Artwork", Farrell et al, 1999, retrieved Apr. 11, 2012 from http://scien.stanford.edu/jfsite/Papers/ImageCapture/ColorChiba.pdf.

"Image-Based Spectral Reflectance Reconstruction Using the Matrix R Method", Zhao et al, Color Research & Application, vol. 32, No. 5, pp. 343-351, Sep. 2007.

"A simplified method of predicting the colorimetry of spot color overprints", Deshpande et al, Proc. 18th Color Imaging Conference: Color Science and Engineering Systems, Technologies, and Applications, pp. 213-216, San Antonio, Texas, 2010.

"Estimating Surface Reflectance Functions from Tristimulus Values", Zuffi et al, retrieved Apr. 11, 2012 from http://www.ivl.disco.unimib.it/papers2003/siof2005-zuffi.pdf.

"Using the Matrix R Method for Spectral Image Archives", Zhao et al, AIC Colour 05—10th Congress of the International Colour Association, retrieved Apr. 11, 2012 from http://citeseerx.ist.psu.edu/viewdoc/download?doi=10.1.1.81.5701&rep=rep1&type=pdf.

"Predicting Spot-Color Overprints: A Quantitative Approach", Husain et al, retrieved Feb. 21, 2012 from http://cias.rit.edu/~gravure/tt/pdf/pc/TT8_Predicting%20Spot-Color%20Overprints.pdf.

"Predicting the colorimetry of spot colour overprints", Deshpande et al, retrieved Feb. 21, 2012 from http://www.google.com/url?sa=t&rct=j&q=&esrc=s&source=web&cd=2&cad=rja&ved=0CDAQFjAB&url=http%3A%2F%2Fwww.color.org%2FDigitalPrint%2FDeshpande_overprints.pdf&ei=VnLxUfa3FoipigKuooAw&usg=AFQjCNGvozlrkm9TO6VWdqWjemrlURx8Dg& sig2=3tLj1-u7Gbiks2eWLQoLow&bvm=bv.49784469,d.cGE.

EPO Search Report for European Application No. 13 17 3921 dated Nov. 4, 2014.

* cited by examiner

US 9,347,874 B2

CALCULATING THE SPECTRAL CHARACTERISTICS OF THE COLOR RESULTING FROM OVERLAYING COLORANTS

RELATED PATENT APPLICATIONS

This invention claims benefit of priority of U.S. Provisional Patent Application No. 61/639,718 filed 27 Apr. 2012 to inventors Keydar, et al., titled "CALCULATING THE SPECTRAL CHARACTERISTICS OF THE COLOR RESULTING FROM OVERLAYING COLORANTS," the contents of which are incorporated herein by reference.

COPYRIGHT & TRADEMARK NOTICES

Certain marks referenced herein may be trademarks or registered trademarks of third parties. Use of these marks is solely for providing an enabling disclosure by way of example and is not to be construed as limiting the scope of this invention to material associated with such trademarks.

FIELD OF THE INVENTION

The present disclosure relates generally to color printing.

BACKGROUND

Accurate calculation of the color that results from overprinting a set of colorants, also called inks herein, is a recognized important problem in the graphic arts.

In the printing industry, there are the standard process inks cyan (C), magenta (M), yellow (Y), and black (K), and red (R), green (G), blue (B) colorants. Today, sometimes more than four inks are used, and the additional inks for printing are typically orange (O), violet (V), and green (G). A spot color is a color made by a single ink, such ink being a pure ink or itself made from mixing a plurality of inks. One example of a spot color is a PANTONE® color. There is a need in the art to accurately predict the spectral characteristics, e.g., the reflectance of an overprint of inks, e.g., process inks and/or spot colors. There is also a need in the art to spectrally characterize spot colors, for example for determining a profile for use in color management, for example to characterize a device that prints using such spot colors on a particular substrate, or for characterizing a device that can reproduce a spot color using an overprint of several colorants on the particular substrate.

DESCRIPTION OF EXAMPLE EMBODIMENTS

Figure 1:
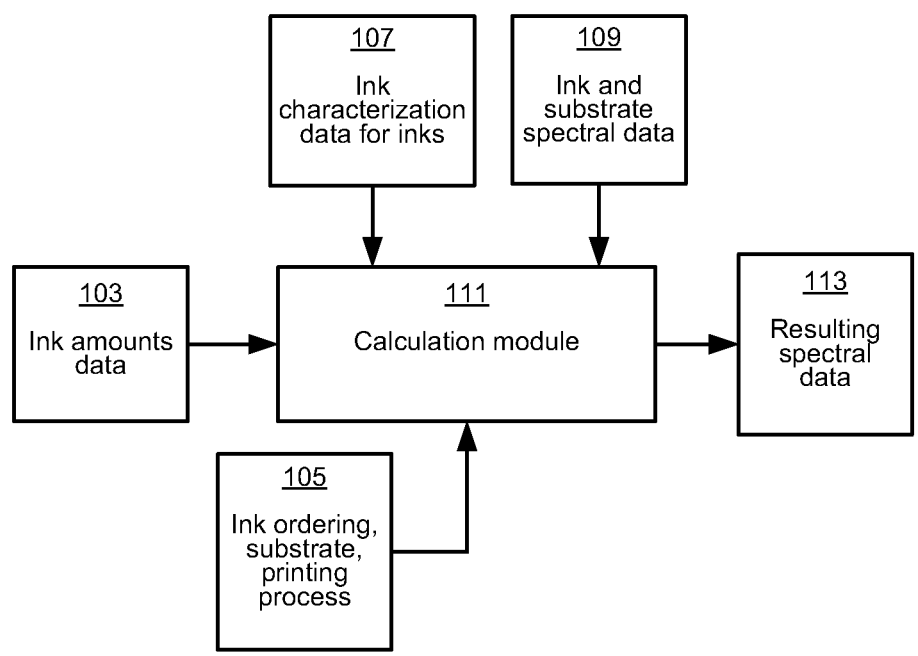
FIG. 1 shows an embodiment of a method of the present invention that determines on a processing apparatus a spectral measure of an overprint of a plurality of inks.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be used without departing from the principles described herein.

Overview

Embodiments of the present invention include a method, an apparatus, and logic encoded in one or more computer-readable tangible media to carry out a method. The method is to spectrally characterize a colorant printed on a substrate of interest using a printing process of interest, such characterizations suitable for determining a spectral measure of the reflectance of an overprint of several so-characterized inks. The method further is to determine on a processing apparatus, e.g., on a computer, a spectral measure of the reflectance of an overprint of several inks made on the substrate using the printing process. The method of spectrally characterizing an ink usable for spectrally characterizing overprints uses test prints of either the inks, or in some embodiments, standard process inks. By using spectral characterizations, and by calculating the spectral measure of the reflectance of an overprint, one has a full description of the color of the overprint, independent of observer and illuminant.

So characterizing inks, and determining the spectral measure of an overprint is useful to make hard-copy proofs of a print, and further to determine a display that matches the appearance of an overprint, called soft-proofing.

Existing color technology used by a majority of products characterizes inks and overprints thereof by sampling a relatively large number of overprints to determine points in a device dependent color space, e.g., by amounts of the inks used by the device using a particular printing process on a particular substrate to determining the color of the overprints in a device independent color space, e.g., CIE-LAB or CIE-XYZ, and defining mappings between the device independent space, e.g., amounts of inks, and the device dependent color space for a number of points. Modern color management systems use such profiles to enable transforming between a device dependent color space, e.g., that of a scanner or camera in the case of an input device, to a three-dimensional device independent color space, e.g., CIE-LAB or CIE-XYZ. Such color management systems further transform from the device independent color space to an output device space, e.g., a printer on a substrate of interest, a printing process of interest on the substrate of interest, or a particular display. In the case of a printing device or technique, there may be three or more inks used. The profile includes mappings from one color space to another color space for a number of points, and typically uses interpolation to determine mappings from points that were not measured. The device independent color space is sometimes called a profile connection space. A mapping from a device space (called the "A" space) to a device independent space (called the "B" space) is commonly called an "AtoB" table, while a mapping from the device independent space to values in a device-dependent color space are commonly called a "BtoA" table. A typical profile includes several such mappings depending on the intent. Colorimetric intent is meant to convey the exact device color behavior, without any gamut mapping, and is typically used to store a device's behavior. When such tables are referred to herein, they are colorimetric intent tables.

A fundamental measure of a color is the spectral measure, e.g., reflectance as measured by a photospectrometer. Typical photospectrometers measure a spectral measure of reflectance proportional to the spectrum of the reflected light as a function of wavelength, e.g., at a number of wavelengths in the visible spectrum of 380 to 730 nm. Some spectrometers measure at 36 wavelengths in the visible spectrum range.

Particular embodiments include a method of operating a processing apparatus to determine a spectral measure of reflectance of an overprint of a plurality of inks made on a substrate using a printing process. The method comprises accepting in the processing apparatus a spectral measure of reflectance of a substrate at a plurality of wavelengths and accepting in the processing apparatus a pre-defined order of printing an overprint of a plurality of inks on the substrate. The method further includes, for each ink of the plurality of inks, for a respective amount of printing of the ink, accepting or determining in the processing apparatus a respective interaction of absorption and reflection function ("IAR function") indicative of how the ink interacts with a layer of one or more other inks when printed over the layer of the one or more other inks. The method includes determining in the processing apparatus the spectral measure of reflectance of the overprint of the plurality of inks printed on the substrate in the pre-defined order in the respective amounts of the inks, including repeatedly multiplying, in the pre-defined order, for each additional ink added to a partial overprint of the inks before the additional ink is added, the spectral measure of the partial overprint by the exponentiation of (i) the ratio of the spectral measure of the additional ink on the substrate to the spectral measure of the substrate, by (ii) the IAR function of the additional ink, starting with spectral measure of the substrate.

In some versions, the determining of the spectral measure is for a plurality of wavelengths.

Particular embodiments include a method of operating a processing apparatus to characterize an ink when printed over a second ink on a substrate using a printing process. The method comprises accepting in the processing apparatus: a spectral measure of reflectance of the substrate, the spectral measure being at a plurality of wavelengths; the spectral measure of reflectance of the ink printed on the substrate; and the spectral measure of reflectance of a first background printed on the substrate. The method further comprises accepting or determining in the processing system the spectral measure of reflectance of the ink printed on the first background; and determining in the processing system an IAR function usable for determining the spectral measure of an overprint of the ink over an overprint of two or more other inks by multiplying the spectral measure of reflectance of the overprint of the of two or more other inks by the exponentiation of (i) the ratio of the spectral measure of the ink on the substrate to the spectral measure of the substrate, by (ii) by the IAR function of the ink.

In some versions, the determining of the spectral measure is for a plurality of wavelengths.

Particular embodiment includes a non-transitory computer-readable medium with a set of instructions thereon that when executed by one or more processors of a processing system cause carrying out a method as described in this Overview section.

Particular embodiment includes an apparatus comprising one or more processors and storage, the storage comprising instructions that when carried out by one or more of the processors carry out a method as in this Overview section.

Particular embodiments may provide all, some, or none of these aspects, features, or advantages. Particular embodiments may provide one or more other aspects, features, or advantages, one or more of which may be readily apparent to a person skilled in the art from the figures, descriptions, and claims herein.

Example Embodiment

Embodiments of the invention relate to a well-recognized problem in the graphic arts industry: how to determine, in advance of printing, the color that results from an overprint, printed using a printing process of interest, of a plurality of inks printed in a pre-defined order, one on top of the other, on a substrate of interest. These inks can be of any color, i.e., from anywhere in a pre-defined color space. By so determining the color that results from an overprint, prior to printing, e.g., prior to production of a print run, one can simulate the final result of printing on a proofing device, or display the expected final result of printing on a display device acting as a so-called soft proofer.

The most accurate way to describe a printed color is by the spectrum of the light when the color is reflected.

Embodiments of the invention include a method to characterize an ink, e.g., obtain a profile for the ink. The method includes printing a number of test prints using the ink on a substrate of interest. Embodiments of the method further include measuring spectral data, in particular, a spectral measure of reflectance of at least some of the test prints, and determining a set of a relatively small number of spectral parameters from the measured spectral data to characterize the ink. Embodiments of the invention also include a method of using the determined set of parameters to calculate the color, in a spectral domain, of an overprint of the characterized ink laid on top of an overprint of one or more other inks using a printing process of interest. Each of the one or more other inks has a known or determined set of spectral parameters to characterize the other ink.

One feature of embodiments of the method is that all calculations can be carried out in spectral coordinates. On one set of embodiments, the spectral coordinates are spectral quantities each at a number of wavelengths, e.g., at 36 wavelengths, so that a full description of a color is always available in a device independent form, e.g., independent of the human observer and the illuminant.

The method of determining the color of an overprint of a plurality of inks is applicable sequentially, one ink layer at a time, so that by applying the method of determining a resulting color by overprinting an additional ink to an existing overprint of two or more inks whose color has been determined, e.g., using an embodiment of the method of the invention, the resulting color of the overprint of the plurality can be obtained, no matter how many inks in the plurality.

It is common, e.g., in color management systems, to determine the color of overprints by carrying out interpolation in a device independent color space such as CIE-LAB or CIEXYZ. Such methods are typically used for characterizing subtractive printing using CMYK or RGB colorants. In contrast, embodiments of the present invention carry out calculations in the spectral domain using the measured data for the colorant and a spectral characterization of the ink. Therefore, methods of the present invention are readily suitable for characterizing prints of two or more inks which may or may not include the common process inks CMYK, or which may or may not include RGB inks.

In contrast, methods of the present invention can provide a spectral measure of the reflectance of an overprint of the inks. Methods of the present invention include characterizing the spectral behavior of an ink, including interaction with other ink(s) over which the ink is printed. Methods of the present invention are suitable for calculating the spectral measure of the reflectance of an overprint of the inks, and hence the color of the inks. The inks may be CMYK, RGB, CMYK with one or more spot colors, 7-color printing, sever-color printing with one or more spot colors, and so forth, A Method of Determining the Spectral Measure of an Overprint FIG. 1 shows an embodiment of a method of the present invention that determines on a processing apparatus a spectral measure of an overprint of a plurality of inks. The method includes a calculation module 111, e.g., operating on the processing apparatus, accepting information 105 on the ink ordering, the printing process, and substrate. The calculation module accepts ink amounts 103 for the set of inks for the ordering, and uses spectral data 109 for each of the inks and for the substrate, and data 107 that spectrally characterizes each of the inks to calculate a resulting spectral measure 113 of an overprint of the inks in the order in the ink amounts.

Providing the Data 109 on Individual Inks and the Substrate

Denote by n the number of inks applied and by $P_1$, $P_2$, $P_3$, ..., $P_n$ a set of n inks, each of which may be one of the standard process colors C, M, Y, or K (cyan, magenta, yellow, or black) or a spot color.

To profile the behavior of a plurality of these process and/or spot color inks when printed in a specific order using a printing process of interest on a substrate of interest, one can print charts using one or more of the inks, and measure the spectral property, e.g., the reflectance of different parts of the charts as a function of wavelength, e.g., using a spectrophotometer. These form the ink and spectral data 109.

The reflectance of a surface is denoted by a function R of wavelength denoted $\lambda$. Spectral measures are determined and calculated in embodiments of the invention for a number, denoted L, of wavelengths. In one embodiment, L=36. Denote the L wavelengths by $\lambda_j$, j=0, 1, ..., L−1. For simplicity of notation, each wavelength, $\lambda_j$ is referred to simply by an index j, j=0, 1, ..., L−1, so that, e.g., for L=36 wavelengths, the wavelengths $\lambda_0, \lambda_1, ..., \lambda_{35}$ are denoted by the respective index 0, 1, ..., L−1. Denote by R(j), j=0, 1, ..., L−1 a spectral measure, e.g., the reflectance as measured by a by a spectrophotometer at these L wavelengths.

Denote the substrate's spectral measure by $R_0(j)$, j=0, 1, ..., L−1. This may be measured, e.g., by a spectrophotometer, or provided, e.g., by a manufacturer as a characterization of the substrate, and forms part of data 109.

Consider the inks denoted $P_i$, i=1, 2, ..., n, each of which can be a process ink (C, M, Y, or K) or a spot color ink. Denote by $d_i$ i=1, 2, ..., n the respective amounts of inks $P_i$, i=1, 2, ..., n that are to be printed on the substrate, and denote by $R(d_i; j)$ the L spectral values of $d_i$ amount of ink Pi, i=1, n and j=1, ...L−1 printed directly on the substrate. The $R(d_i; j)$ form part of data 109.

Characterization 107

Embodiments of the invention characterize each ink by the ratio of its spectral measure when printed in various amounts on a substrate of interest to the spectral measure of the substrate, and by an IAR (interaction of absorption and reflection) function that is a property of the ink indicative of how various amounts of the ink interact in various amounts when printed over another ink layer or plurality of ink layers.

Calculation Module 111 Determining the Spectral Measure of an Overprint

Figure 2:
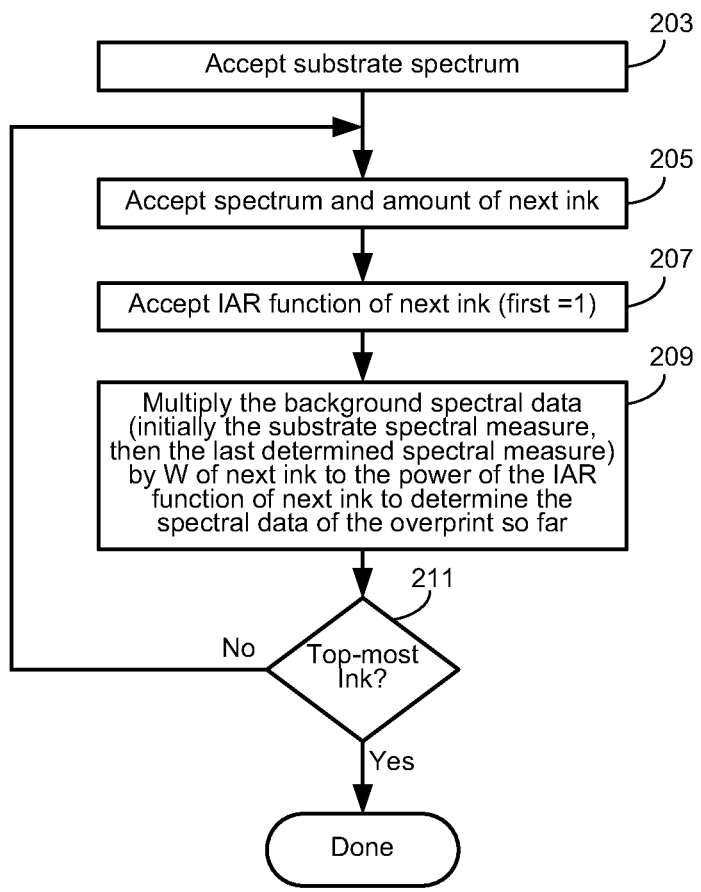
FIG. 2 shows a flowchart of one embodiment of determining the spectral measure of an overprint as carried out by the calculation module of FIG. 1.

FIG. 2 shows a flowchart of one embodiment of determining the spectral measure of an overprint as carried out by the calculation module 111. The method includes in 203 accepting the spectral measure of the substrate, which initially is the background. For each additional ink, in the order of printing starting with the first ink that is printed directly on the substrate, the method includes in 205 accepting the spectral measure of the next ink in the amount of the next ink, accepting in 207 the IAR function of this next ink in its amount when printed on the current background. Initially, for the first ink, the IAR function is 1. Step 209 includes determining the current spectral measure by multiplying the current background's spectral measure, which initially is the substrate's spectral measure and thereafter is the spectral measure of all layers printed but this next measure, by the ratio (from 109) of the spectral measure of this next ink printed on the substrate to the spectral measure of the substrate, such ratio exponentiated by the IAR function of the next ink printed on the current background. In 211, it is determined if this next ink is the top-most ink, in which case the process is terminated with the final spectral measure being the current spectral measure from step 209, otherwise the process continues with a new next ink, with the current spectral measure from step 209 becoming the new background.

In more detail, assume there are n inks denoted $P_1$, $P_2$, ..., $P_n$. Denote by Order($P_1, P_2, ..., P_n$) the order of printing. In this case, the order is print $P_1$, then $P_2$, etc., then $P_n$. Such an order is denoted as $P_1 \leftarrow P \leftarrow ... \leftarrow P_n$. Some of the inks may be the process inks CMYK, and some of the inks also may include orange (O), violet (V), and green (G), often used for printing with more than 4 inks. One or more of the inks may be spot colors.

Spectral measures are determined and calculated in embodiments of the invention for a number, denoted L, of wavelengths. In one embodiment, L=36. Denote the L wavelengths by $\lambda_j$, j=0, 1, ..., L−1. For simplicity of notation, each wavelength, $\lambda_j$ is referred to simply by an index j, j=0, 1, ..., L−1, so that, e.g., for L=36 wavelengths, the wavelengths $\lambda_0, \lambda_1, \ldots, \lambda_{35}$ are denoted by the respective index 0, 1, ..., L−1. Denote by R(j), j=0, 1, ..., L−1 a spectral measure, e.g., the reflectance as measured by a spectrophotometer at these L wavelengths.

Denote the substrate's spectral measure by $R_0(j)$, j=0, 1, ..., L−1. This may be measured, e.g., by a spectrophotometer, or provided, e.g., by a manufacturer as a characterization of the substrate.

One aspect of the invention is determining the spectral measure, denoted $R(d_1, d_2, d_n; j)$, j=0, ..., L−1, of an overprint of a number, denoted n, of inks $P_1, P_2, \ldots, P_n$ laid (printed) in a predefined order, denoted $\text{Order}(P_1, P_2, \ldots, P_n) = P_1 \leftarrow P_2 \leftarrow \ldots \leftarrow P_n$, in relative quantities, denoted $d_1, d_2, d_n$ for the inks $P_1, P_2, \ldots, P_n$, respectively, on the substrate of spectral measure $R_0(j)$, j=0, 1, ..., L−1.

In one embodiment, the spectral measure $R(d_1, d_2, \ldots, d_n; j)$ for the overprint of n inks is determined by repeated multiplication, in the order of printing, by the exponentiation of the ratio of the spectral measure of the additional ink to the spectral measure of the substrate by the IAR function, starting with the substrate's spectral measure $R_0(j)$. The IAR function is a function of at least the amount of ink and the wavelength. That is, denoting the IAR function for ink $P_i$, by $IAR(d_i; j)$ where $d_i$ is the amount of ink $P_i$, e.g., as a density or percentage, being printed, and j is the index for the wavelength, the spectral measure is $$R(d_1, d_2, \ldots, d_n; j) = R_0(j) \times W(d_1; j)^{IAR(d_1; j)} \times W(d_2; j)^{IAR(d_2; j)} \times W(d_n; j)^{IAR(d_n; j)}$$
for j=0, 1, ..., L−1, where:
× denotes multiplication,
$W(d_i, j) = R(d_i; j)/R_0(j)$, i=1, ..., n, and j=1, ... L−1, the ratio of the spectral measure of the ink $P_i$ printed on the substrate to the spectral measure of the substrate,
$R(d_i; j)$ are L spectral values of $d_i$ amount of ink Pi, i=1, ..., n and j=1, ... L−1 printed on the substrate, and
$R_0(j)$ are the L spectral values for the substrate, j=1, ... L−1.

In one embodiment, the spectral measure $R(d_1, d_2, \ldots, d_n; j)$ for the overprint of n inks is determined as if the uppermost ink, $P_n$ is printed on a background which is an overprint of n−1 inks on the substrate, such overprint, now considered a background, having a spectral measure $R(d_1, d_2, \ldots, d_{n-1}; j)$, by multiplication of $R(d_1, d_2, \ldots, d_{n-1}; j)$ by the exponentiation of the ratio of the spectral measure of the uppermost ink $P_n$ to the spectral measure of the substrate by the IAR function $IAR(d_n; j)$ of the uppermost ink $P_n$. That is, $$R(d_1, d_2, \ldots, d_n; j) = R(d_1, d_2, \ldots, d_{n-1}; j) \times \left(\frac{R(d_n; j)}{R_0(j)}\right)^{IAR(d_n; j)}$$

for j = 1, ..., L−1.

Note that for the ink printed on the substrate itself, IAR=1 for all wavelengths and ink amounts.

Determining the IAR Function

It is clear from the above that one feature of the method of determining the spectral measure of an ink is considering each additional layer as being printed on a background, be it a background of a single ink layer or of a plurality of ink layers, and determining the spectral measure of the overprint from the spectra of the background and the substrate, and the IAR function. Thus, one aspect of the invention is determining the IAR function of an ink $P_i$ when printed on a particular background, that background being either a single ink layer or a plurality of ink layers.

Different embodiments of the invention use spectral measures of reflectance made on one of at least four types of readily available or obtainable test data:

Data set 1) Prints of various coverage amounts of the ink $P_i$ on a white background, i.e., the substrate of interest, a gray background, in one embodiment assumed to be 50% coverage amount of black, and a black background, in one embodiment assumed to be 100% coverage of black ink on the substrate of interest. See, for example, U.S. Pat. No. 5,933,578 to van de Capelle et al, titled "METHOD AND DEVICE FOR DETERMINING THE COLOR APPEARANCE OF COLOR OVERPRINTS," the contents of which are incorporated herein by reference.

Data set 2) Overprint charts made with a set of inks, of which one is the ink of interest $P_i$. In particular, overprints at various amounts, e.g., so-called step wedges the ink $P_i$ on the substrate of interest and overprints of two inks, the latter being the ink $P_i$ on a print of a second ink on the substrate of interest.

Data set 3) An overprint chart for process inks, e.g., C, M, Y, K, such as a chart conforming to the European Color Initiative (ECI) ECI2002 test target available 2 Mar. 2012 at www~dot~ECI~dot~org/en/downloads, where ~dot~ denotes a period (".") in the actual Web address, a chart conforming to the American National Standards Institute ANSI/IT8.7/4 (currently in review), or the earlier ANSI/IT8.7/3:1993, standardized as ISO 12642:1996 and titled "Graphic technology—Input data for characterization of 4-color process printing," or some similar overprint chart. In addition, for any non-process inks, data such as Data set 1 above, that is, prints of various coverage amounts of the non-process ink on a white background, a gray background, and a black background.

Data set 4) Just a single 100% coverage amount patch of the ink $P_i$ printed by a printing process of interest on a substrate of interest. Using this data includes also using a database of pre-defined IAR functions for the printing process (or similar) for the substrate (or similar), previously determined. In one example, IAR functions determined for C, M, and Y per the Data set 3 above are pre-stored in a database. An improved version of Data set 4 includes various coverage amounts of the ink $P_i$ made by the printing process of interest on the substrate of interest.

Different embodiments furthermore use different methods of determining the IAR function using these data sets.

Consider an ink $P_a$ at an amount $d_a$ printed using the printing process on a background printed using the printing process on the substrate. Because the spectral measure can be determined as if the background was a single ink, for the sake of the formulae, denote the background as an ink $P_b$ at an amount $d_b$. Then $$R(d_b, d_a; j) = R(d_b; j) \times \left(\frac{R(d_a; j)}{R_0(j)}\right)^{IAR(d_a; j)},$$

So that $$IAR(d_a; j) = \frac{\log R(d_b, d_a; j) - \log R(d_b; j)}{\log R(d_a; j) - \log R_0(j)}$$

wherein the log is to any base, e.g., base 10 or base e.

The above expression for $IAR(d_a; j)$ can be manipulated to give the following expression in terms of ratios of spectra:

$$IAR(d_a; j) = \frac{\log R(d_b, d_a; j) - \log R_0(d_b; j) - \log W(d_b; j)}{\log W(d_a; j)}$$

These expressions can be used in different ways in different embodiments to determine the IAR function, depending on the spectral measure already available.

Use of Data Set 1

For any ink of interest, for a printing process of interest and a substrate of interest, the data set includes the spectral measure of the substrate (denotes this $R_0(j)$), the spectral measure of a first background, e.g., a gray background (denote this $R(d_g; j)$), spectral measure of the ink at various amounts on the raw substrate (denote this $R(d_a; j)$), and the spectral measure of the ink at various amounts printed on the first, e.g., gray background (denote this $R(d_g, d_a; j)$).

Figure 3:
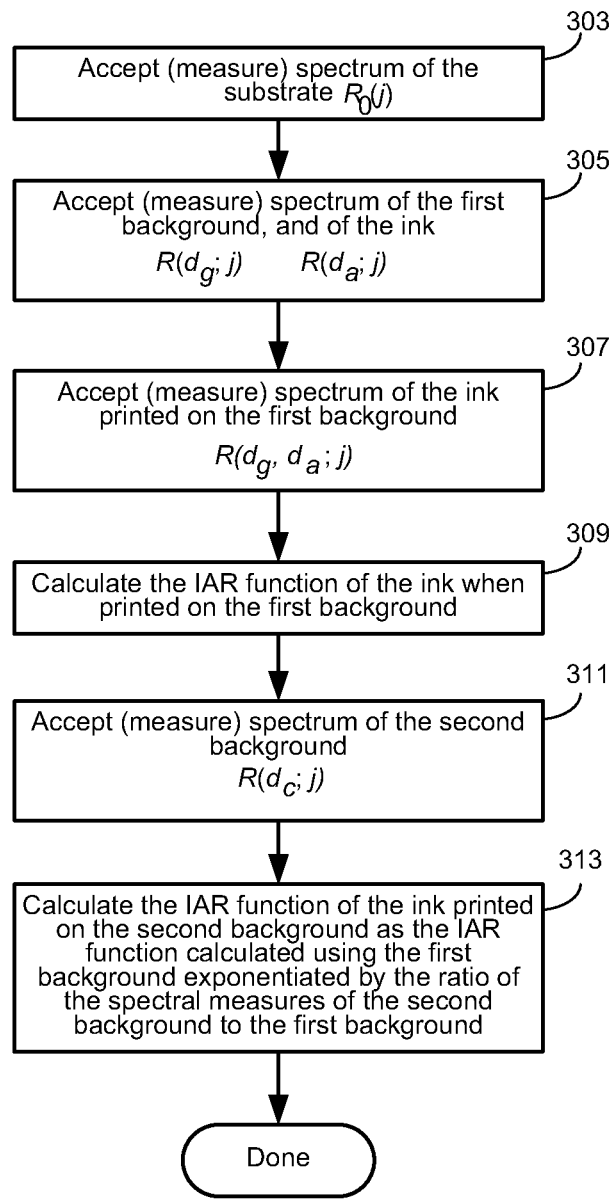
FIG. 3 shows a flowchart of one embodiment of determining an IAR function for an ink at a particular amount printed using a printing process on a background printed using the printing process on the substrate.

FIG. 3 shows a flowchart of one embodiment of determining the IAR function for an ink $P_a$ at an amount $d_a$ printed using the printing process on a background printed using the printing process on the substrate. The method includes in 303 accepting or accepting and measuring the spectral measure (spectrum, reflectance) of the substrate $R_0(j)$ and in 303 accepting or measuring the spectral measures (spectra, reflectances) of the first, e.g., gray background $R(d_g; j)$ and of the ink in amounts $d_a$ on the spectrum, denoted $R(d_a; j)$. Step 307 includes accepting or measuring and accepting the spectral measure of various amounts denoted $d_a$ when printed on the first background, this denoted $R(d_g, d_a; j)$.

Step 309 calculates the IAR function for the ink $P_a$ at various amounts $d_a$ when printed on the first, e.g., gray background for the wavelength indices $j=1, \ldots, L-1$, using, e.g., Using $$IAR(d_a; j) = \frac{\log R(d_g, d_a; j) - \log R(d_g; j)}{\log R(d_a; j) - \log R_0(j)}.$$

Note that while the above used the prints on the gray background as an example of the first background, the prints on any first background may be used.

An improved embodiment includes steps 311 and 313, and uses a slightly modified model for the IAR function, in which the IAR function varies with differing backgrounds. Consider a first background, e.g., the gray background per Data set 1, denoted, as above, by $P_g$ at an amount $d_g$. Consider a second background, denoted $P_c$ in an amount $d_c$. This second background, for example, can be the layers of inks up to the present new layer. That is, the $P_c$ and $d_c$ are for notational convenience only. The second background may be, for example, the last ink of the layers prior to the present ink of interest, such last ink being printed directly on the substrate. There need not be an actual ink in such an amount. It is desired to determine the IAR function for the additional ink layer $P_a$ at an amount $d_a$ printed over the second background.

Denote by $IAR(d_a; j)|_g$ the IAR function as determined on the first background, e.g., from the first data set for ink on a gray background, and denote by $IAR(d_a; j)|_c$ the function for ink $P_a$ at an amount $d_a$ printed over the second background. Then, $$IAR(d_a; j)|_g = \frac{\log R(d_g, d_a; j) - \log R(d_g; j)}{\log R(d_a; j) - \log R_0(j)}.$$

The improved method includes, after step 309, in step 311 accepting or accepting and measuring the spectral measure (spectrum, reflectance) of the second background, denoted $R(d_c; j)$. Step 313 includes determining the IAR function for the ink printed on the second background as the IAR function calculated using the first, e.g., gray background exponentiated by the ratio of the spectral measures of the second background to the first, e.g., gray background. That is, $$IAR(d_a;j)|_c = (IAR(d_a;j)|_g) R(d_c;j)/R(d_g;j).$$

All quantities in the right hand side of the above equation are known by measurement, or can be calculated. $IAR(d_a; j)|_g$ is calculated from measurements on data set 1. $R(d_g; j)$ is available by measurement of data set 1. $R(d_c; j)$ is the spectral measurement calculated by application of the main spectral measure equation for all inks but the last ink $P_a$.

Use of Data Set 2

Data set 2 includes making overprints of pairs of all the inks involved. Each pair of inks provides the IAR function of an ink, say $P_a$ at an amount $d_a$ printed using the printing process on a background of an ink $P_b$ printed at an amount $d_b$ using the printing process on the substrate.

For any such pair, $$IAR(d_a; j)|_b = \frac{\log R(d_b, d_a; j) - \log R(d_b; j)}{\log R(d_a; j) - \log R_0(j)}.$$

In one embodiment, the IAR function used in applying the main spectral measure equation is the one for the background last ink printed (the ink $P_b$), e.g., similar to steps 303 to 309 of the method of FIG. 3.

An improved embodiment uses a slightly modified model for the IAR function, in which the IAR function varies with differing backgrounds, as described above for the case of Data set 1, but now using overprints of pairs of the inks of interest, e.g., similar to steps 303 to 313 of the method of FIG. 3.

Again, denote by $P_c$ and $d_c$ the layers of inks up to the present new layer of $P_a$. In a similar manner to the case of the background $P_g$ in quantity $d_g$, using data of an overprint of ink $P_c$ over a print of $P_b$, $$IAR(d_a;j)|_c = (IAR(d_a;j)|_b) R(d_c;j)/R(d_b;j).$$

As in the case of a grey background (Data set 1), all quantities in the right hand side of the above equation are known from measurement or can be calculated. $IAR(d_a; j)|_b$ is calculated from measurements on the overprints. $R(d_b; j)$ is available by measurement on the overprint data set 2. $R(d_c; j)$ is the spectral measurement calculated by application of the main spectral measure equation for all inks but the last ink $P_a$.

Use of Data Set 3

In the case of having overprints of the standard process inks, e.g., using an ECI2002 CMY chart, and the IAR is determined using CMY standard overprints chart measurements using the printing process on a substrate of interest. The CMY charts a device specific color space, which represents a gamut in a device independent color space, e.g., CIE-LAB or CIEXYZ.

The method includes for a background ink $P_b$ printed at an amount $d_b$ and a top ink $P_a$ at an amount $d_a$ printed using the printing process over the background ink, searching in the CMY equivalent background, the top ink $P_a$ printed at an amount $d_a$, determining the resulting spectrum and calculating the IAR for $d_a$ of ink $P_a$ on top of ink $P_b$ from this information.

In general the method includes calculating the IAR function by formula. Needed for this are the spectra of: (1) the substrate, (2) the background (say ink $P_b$ printed at an amount $d_b$ on the substrate), (3) the new ink (say $d_a$ of ink $P_a$ on the substrate), and (4) the new ink printed on the background (say $d_a$ of ink $P_a$ on top of $d_b$ of ink $P_b$).

From these three quantities, one can calculate the IAR.

$$IAR(d_a; j)|_b = \frac{\log R(d_b, d_a; j) - \log R(d_b; j)}{\log R(d_a; j) - \log R_0(j)}.$$

For this, $R(d_b; j)$ is obtained by measuring the spectral measure of a print from the patches. Similarly, $R(d_a; j)$ is obtained by measuring the spectral measure of a print from the patches. Similarly, $R_0(j)$ is obtained by measuring the spectral measure of the substrate. $R(d_b, d_a; j)$ is determined as follows:

(a) Determining the equivalent CMY values of the background ink $P_b$ printed at an amount $d_b$ from $R(d_b; j)$, such CMY denoted by $C(P_b,d_b)$, $M(P_b,d_b)$, and $Y(P_b,d_b)$. This is determined by determining the CIEXYZ values of the spectrum $R(d_b; j)$, and using an BtoA table of the profile for the printing process determined from the ECI2002 (or similar) CMY chart to determine the CMY values of the determined CIEXYZ for CMY process inks for the printing process. Note that for the CMY values, it is assumed that each of C, M, and Y is in the range of 0% to 100%.

(b) Determining the CMY values of the ink $P_a$ printed at an amount $d_a$ from $R(d_a; j)$, such CMY values denoted by $C(P_a,d_a)$, $M(P_a,d_a)$, and $Y(P_a,d_a)$. As for the case of the background ink, this is determined by determining the CIEXYZ values of the spectrum, and using an BtoA table of the profile for the printing process determined from the ECI2002 (or similar) CMY chart to determine the CMY values of the determined CIEXYZ for CMY process inks for the printing process.

(c) Calculating the CMY values of an overprint of the ink $P_a$ over the background ink $P_b$ coverage amount. This is done by adding each of the CMY values and using the minimum of each and the 100% determined C, M, and Y. That is:

$C(P_b,P_a,d_a)=\min\{(C(P_a,d_a)+C(P_b,d_b),100),$ $M(P_b,P_a,d_a)=\min(M(P_a,d_a)+M(P_b,d_b),100)$ and $Y(P_b,P_a,d_a)=\min(Y(P_a,d_a)+Y(P_b,d_b),100),$ where the min(., 100) function assures that the maximum of the C, M, and Y is 100%.

(d) Converting the CMY values of the overprint to a spectrum. This is carried out by using a mapping, e.g., an AtoB table provided by the profile from device dependent CMY to the device independent color space to convert the $C(P_b,P_a,d_a),M(P_b,P_a,d_a),Y(P_b,P_a,d_a)$ to CIE-LAB values then to XYZ values (or directly from CMY to XYZ), then using an XYZ to spectral conversion method. The result is $R(d_b,d_a; j)$.

Figure 4:
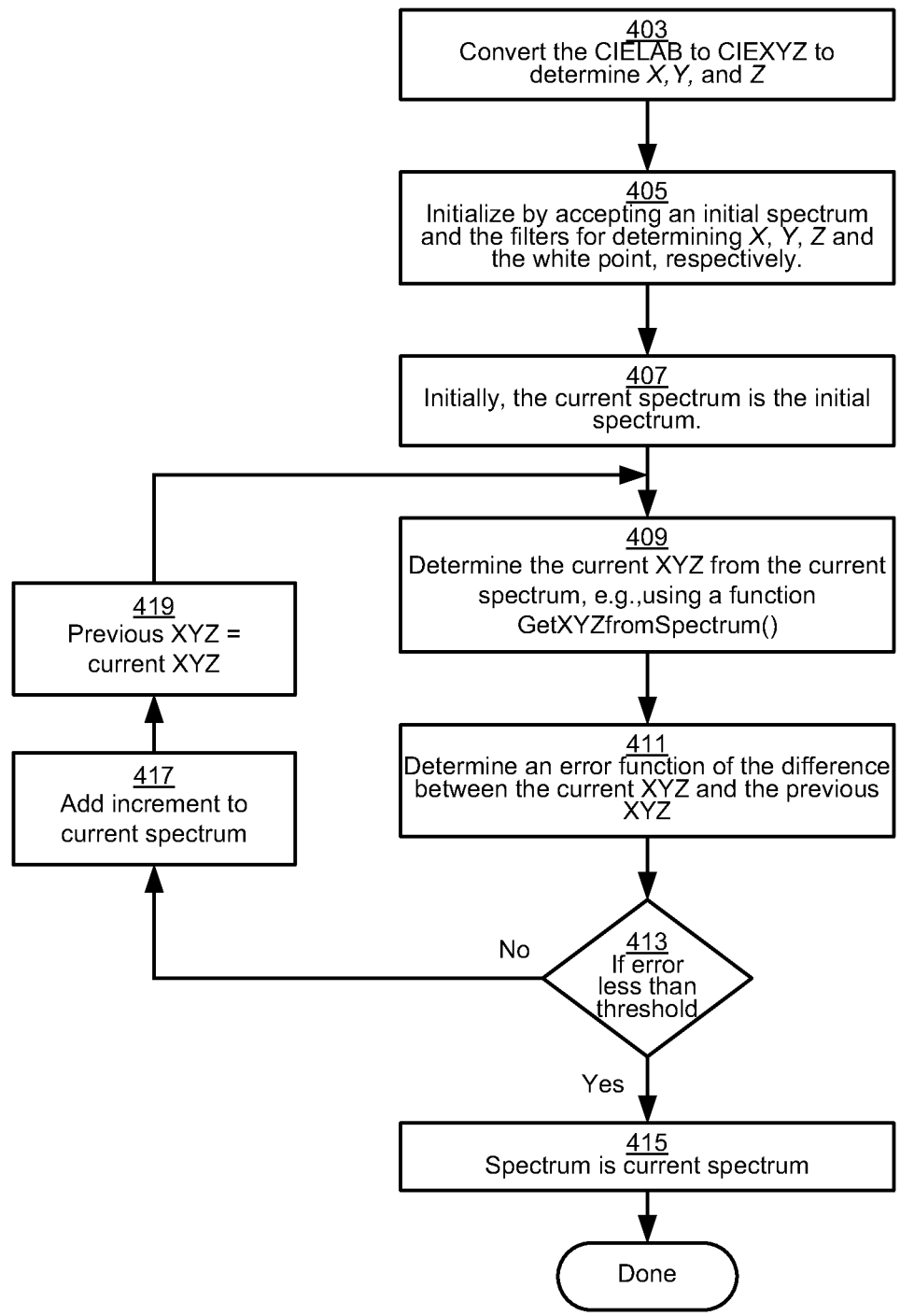
FIG. 4 shows a flowchart of an example embodiment of a method of determining the spectrum of corresponding to a color having a set of CIE-LAB values.

Determining the spectral measure from LAB or XYZ data for step (d) can be carried out by one of several methods. One example is an interactive method. FIG. 4 shows a flowchart of an example embodiment of the method of determining the spectrum of a color having a set of CIE-LAB values.

In step 403 the method includes converting the CIE-LAB to CIEXYZ to determine X, Y, and Z.

In step 405 the method includes initializing by accepting an initial spectrum $R_{init}(j)$ and the filters, denoted $H_X(j)$, $H_Y(j)$, $H_Z(j)$, and $H_W(j)$ for determining X, Y, Z and the white point, respectively.

In step 407, initially the current spectrum denoted $R_{current}(j)$ is the initial spectrum denoted $R_{init}(j)$: $R_{current}(j)=R_{init}(j)$.

Step 409 includes determining the current XYZ, denoted $X_{current},Y_{current},Z_{current}$ from $R_{current}(j)$ e.g., using a function called GetXYZfromSpectrum($R_{current}(j)$) that uses $H_X(j)$, $H_Y(j)$, $H_Z(j)$, and $H_W(j)$.

Step 411 includes determining an error measure of the difference between the current XYZ and the previous XYZ denoted $X_{previous},Y_{previous},Z_{previous}$, e.g., $\Delta E_{XYZ}^2=(X_{current}-X_{previous})^2+(Y_{current}-Y_{previous})^2+(Z_{current}-Z_{current})^2$ Step 413 checks if the error measure is less than a pre-defined threshold, e.g., $\Delta E_{XYZ}^2<\Delta e_T^2$, where $\Delta e_T^2$ is the pre-defined threshold for the error measure $\Delta E_{XYZ}^2$. If so, then in step 415, the spectrum $R(j)=\Delta R_{current}(j)$ and the process terminates.

Otherwise, if the check of step 413 determines that the error measure is not less than the pre-defined threshold, step 417 includes adding an increment to the current spectrum, $R_{current}(j)=R_{current}(J)+\Delta R_{current}(j)$, step 419 makes the previous XYZ values equal to the current XYZ values, $Y_{previous}=Y_{current},Z_{previous}=Z_{current}$, and then the process jumps to step 409.

Other methods of determining a spectrum from values in a device independent color space also are known. One such method determines the spectrum as a weighted sum of basis functions, e.g., orthogonal basis functions. One method uses a weighted sum of so-called principal components. Methods are then used to determine the weights using some error function, e.g., $\Delta E_{XYZ}$ or $\Delta E_{XYZ}^2$, or $\Delta E$ or $\Delta E^2$ determined using LAB.

Use of Data Set 4

Data set 4 includes a database of spectral measures of reflectance made on prints of Data set 1 and/or Data set 2, and/or Data set 3, together with a measurement made on a single print of the ink of interest using the printing process on the substrate, or in the improved version, prints of the ink of interest at various coverage amounts. Thus the database includes pre-stored prototype IAR functions and some measurements to apply to determine an approximation of the IAR function of the ink, say ink $P_a$ printed at an amount $d_a$ printed over a background, say ink $P_b$ printed at an amount $d_b$. Some of the prototype IAR functions can be complete IAR functions determined previously, while others can be approximations of IAR functions, such as piecewise linear functions of wavelength determined by the values of the IAR function at a relatively small number, three or more, of wavelengths.

Figure 6A:
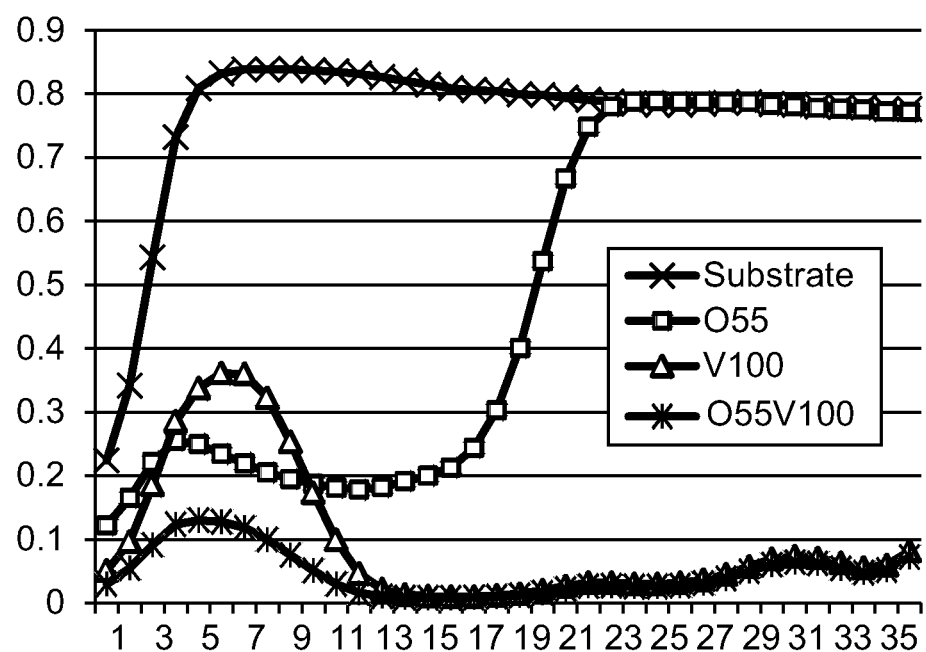
FIG. 6A shows spectral measures obtained using a particular gravure printing process measured for a substrate; 100% coverage of violet on the substrate, 55% orange on the substrate, and 100% coverage of violet printed on top of 55% orange on the substrate.
Figure 6B:
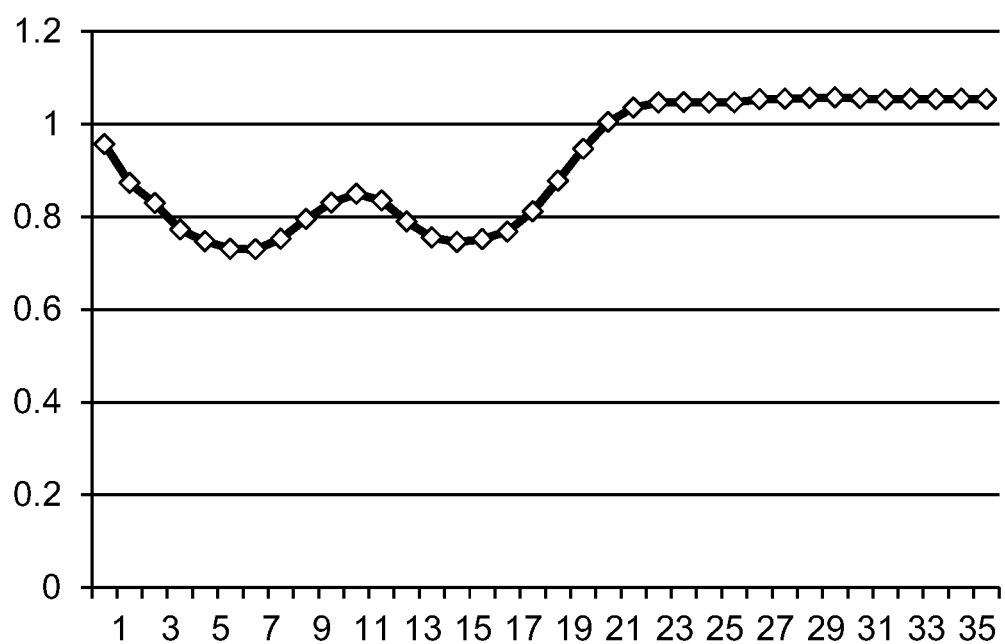
FIG. 6B shows the resulting IAR function for 100% coverage of violet printed on top of 55% orange on the substrate using the particular gravure printing process, determined in accordance with an embodiment of the present invention.

FIG. 6A shows spectral measures obtained using a particular gravure printing process measured for: a substrate; 100% coverage of violet on the substrate, for 55% orange on the substrate, and for 100% coverage of violet printed on top of 55% orange on the substrate. FIG. 6B shows the resulting IAR function for such 100% coverage of violet printed on top of 55% orange on the substrate using the particular gravure printing process. The data of FIG. 6B is an example of the sort of "typical" IAR function that would be stored in the database for using Data set 4.

Simplifications

In some embodiments, each IAR function is approximated by a piecewise linear function of wavelength, defined to be linear between pairs of wavelengths starting with a minimum wavelength, continuing with one or more intermediate wavelengths, and ending with a maximum wavelength.

In one such embodiment, each IAR function is a two-segment piecewise function of wavelength, so that the IAR function is linear between the minimum wavelength and a mid wavelength, and between the mid-wavelength and the maximum wavelength. That is, for ink $P_i$, the IAR function denoted by $IAR(d_i, j)$, is defined by:

$$IAR(d_i, j) = IAR_{min}(d_i) + [IAR_{mid}(d_i) - IAR_{min}(d_i)]/(x_{mid} - x_{min})*x(j) \text{ for } x(j) < x_{mid} \text{ and } j=0, \ldots L-1,$$

$$IAR(d_i, j) = IAR_{mid}(d_i) + [IAR_{max}(d_i) - IAR_{mid}(d_i)]/(x_{max} - x_{min})*x(j) - x_{mid}) \text{ for } x(j) \geq x_{mid} \text{ and } j=0, \ldots L-1,$$

where:

$x(j)$ is the relative distance in the range [0,1] of the j'th wavelength to the whole range of wavelengths, i.e., $x(j) = j/L-1$);

$x_m = 0.0$ corresponds to the minimum wavelength ($j_{min} = 0$);

$x_{mid} = 0.5$ corresponds to the midpoint of the wavelength range ($j_{mid} = (L-1)/2$);

$x_{max} = 1.0$ corresponds to the maximum wavelength ($j_{max} = L-1$,);

$IAR_{min}(d_i)$ is the IAR function for ink $P_i$ in amount $d_i$ at the minimum wavelength ($j=0$; $x=x_{min}$) of the range of wavelengths of interest;

$IAR_{mid}(d_i)$ is the IAR function for ink $P_i$ in amount $d_i$ at the wavelength ($j=L/2-½$; $x=x_{mid}$) that is in the middle of the range of wavelengths of interest; and $IAR_{max}(d_i)$ is the IAR function for ink $P_i$ in amount $d_i$ at the maximum wavelength ($j=L-1$; $x=x_{max}$) of the range of wavelengths of interest.

For embodiments in which the IAR function is a two-segment piecewise linear function of wavelength, three parameters are determined: $IAR_{mm}(d_i)$, $IAR_{mid}(d_i)$, and $IAR_{max}(d_i)$. These parameters can be determined in various ways from spectral measures of reflectance or from data characterizing the particular inks, e.g., Data sets 1, 2, and 3 as described above.

Figure 7:
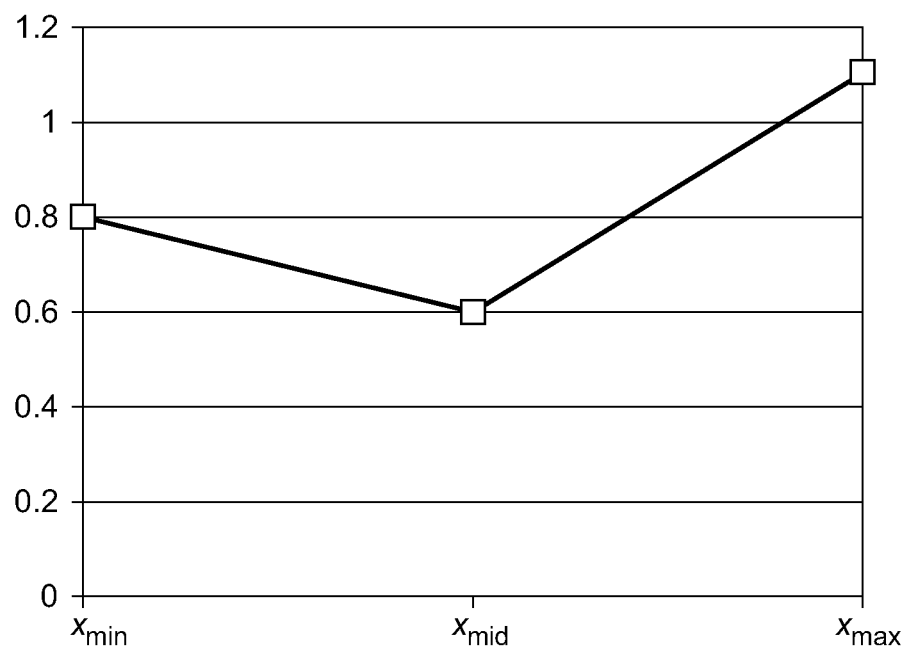
FIG. 7 shows an example of a two-segment piecewise linear IAR function of an ink determined in accordance with an embodiment of the present invention.

FIG. 7 shows a typical two-segment piecewise linear IAR function of an ink.

In yet another embodiment, three piecewise linear segments are used to approximate the IAR function.

In yet another embodiment, more than three piecewise linear segments are used to approximate the IAR function.

A Processing System

Figure 5:
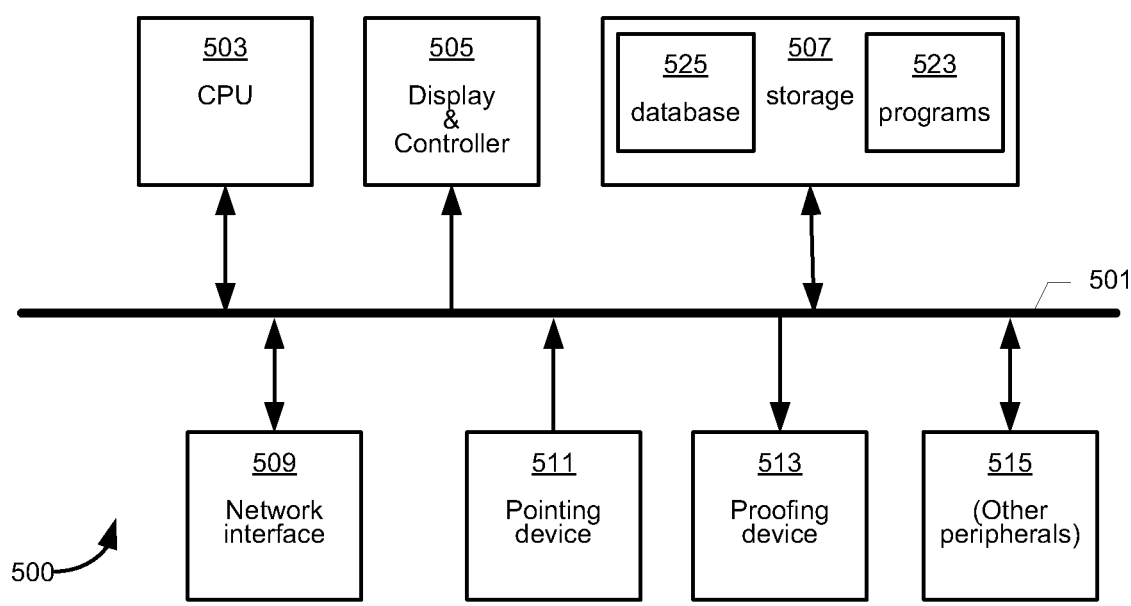
FIG. 5 shows a processing system, e.g., a computer in which embodiments of the present invention may be implemented, e.g., in which the functions of the calculation module are carried out, and which can carry out the methods described by one or more of the flowcharts of FIG. 2, FIG. 3, and FIG. 4.

FIG. 5 shows a processing system 500, e.g., a computer in which embodiments of the present invention may be implemented, e.g., in which the functions of the calculation module 111 are carried out, and which can carry out the methods described by one or more of the flowcharts of FIG. 2, FIG. 3, and FIG. 4. The processing system of FIG. 5 includes a central processing unit (CPU) and storage 507, including memory for the processing system which may include memory embedded in a semiconductor device, or a separate memory subsystem including main RAM and/or a static RAM, and/or ROM, and also cache memory. Storage 507 may include one or more other storage elements, such as magnetic and/or optical and/or or further solid state storage devices. The processing system 500 includes a bus subsystem 501 for communicating between the components. For simplicity, the bus subsystem 501 is shown as a simple bus, and those skilled in the art will understand that a modern bus subsystem includes several bus subsystems, not shown for simplicity of exposition. The processing system 500 may further include one or more network interface devices, one such device 509 shown in the drawing. For display purposes, the processing system 500 may include a display and controller 505, that includes e.g., a liquid crystal display (LCD), organic light emitting display (OLED), a cathode ray tube (CRT) display, or some other display. More than one display may be included, or for some applications, no display may be included. For user interaction, the processing system may include a pointing device 511. When used for proofing, the processing system 500 may be coupled to a proofing device 513. Other peripherals 515 may be included.

While FIG. 5 shows one processing system, the methods can be carried out by more than one processing system, each of which can have more than one CPU or similar element. Furthermore, the processing system may be a distributed processing system with processors coupled by a network, e.g., via network interface devices that may include a wireless network interface devices.

The storage 507 forms a computer-readable storage medium. In some embodiments, the computer-readable storage medium 507 includes a database 525 comprising IAR functions, data for printing charts, e.g., ECI2002 or other charts per Data set 1 and/or Data set 2, and/or data per Data set 4. Database 525 may further comprise previous spectral measures of reflectance. The computer-readable storage medium further includes instructions that when executed on the processing system carry out one or more of the methods described herein.

Embodiments of the present invention include an apparatus such as shown in FIG. 5 comprising one or more processors and storage, the storage comprising instructions that when carried out by one or more of the processors carry out any of the methods described herein of determining a spectral measure of an overprint of a plurality of inks printed on a substrate using a printing process.

Examples

Consider as some examples, a particular gravure printing system with the first ink Orange (O), the second ink violet (V), and the third ink green (G), that is a printing order O←V←G, on a particular substrate.

Figure 8:
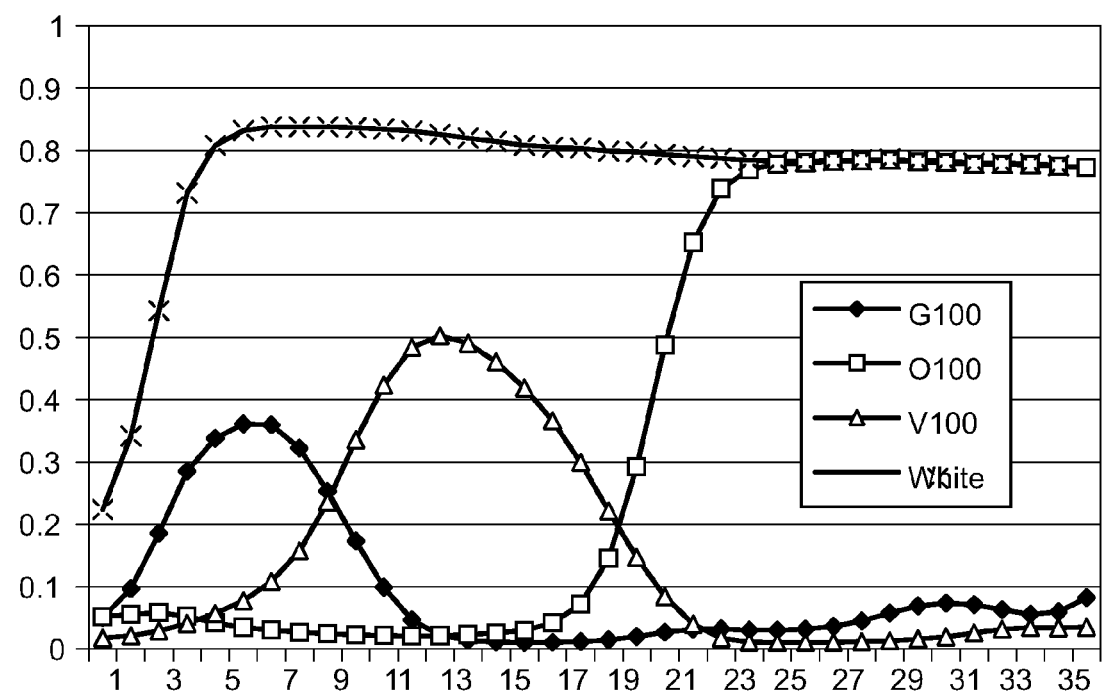
FIG. 8 shows 36 spectral measures of reflectance for a substrate and for orange (O), violet (V), and green (G) each printed in 100% amounts on the substrate.

FIG. 8 shows 36 points of spectral measures of reflectance for the substrate and for O, V, and G each printed in 100% amounts on the substrate.

Figure 9A:
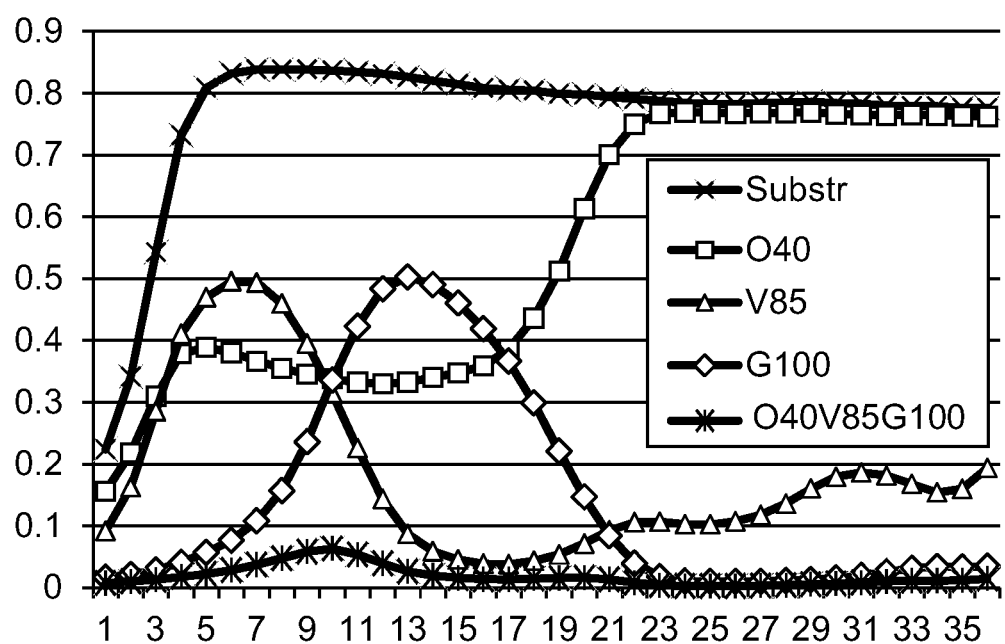
FIG. 9A shows an example of the measured reflectance spectra of the substrate and of V at 85%, O at 40%, and G at 100%, as well as the spectral measure of reflectance, calculated in accordance with an embodiment of the invention, of an overprint of 85% V, 40% O, and 100% G in the printing order orange, then violet, then green.

FIG. 9A shows a second example the measured spectra of the substrate and of V at an amount 85%, O at 40%, and G at 100%, as well as the spectral measure, calculated in accordance with an embodiment of the invention, of an overprint of 85% V, 40% O, and 100% G in the printing order O←V←G. The actual spectrum of an overprint also was measured, and a measure of the color difference ΔE between the calculated and measured colors was determined, as $$\Delta E = \sqrt{(L_{calc} - L_{meas})^2 + (a_{calc} - a_{meas})^2 + (b_{calc} - b_{meas})^2},$$

where $L_{calc}, a_{calc}, b_{calc}$ and $L_{meas}, a_{meas}, b_{meas}$ are the calculated CIE-LAB values and measured CIE-LAB values, respectively, of the overprint, whose calculated spectrum is shown in FIG. 9A and determined according to an embodiment of the invention. For this example, the color difference ΔE was determined to be 2.3.

Figure 9B:
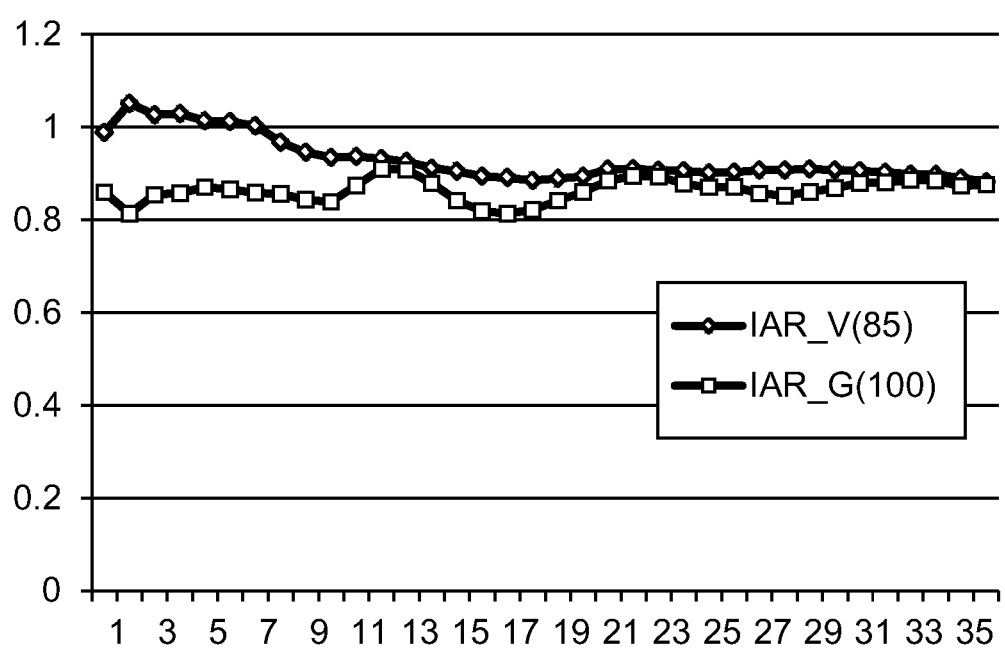
FIG. 9B shows the IAR functions for the violet (V) ink at 85% coverage and the green (G) ink at 100% coverage, used to determine the overprint spectrum of FIG. 9A in accordance with an embodiment of the present invention.

FIG. 9B shows the IAR functions for the violet (V) ink at 85% coverage and the green ink at 100% coverage, used to determine the overprint spectrum of FIG. 9A. Note that the IAR for the first ink (in this case orange) is always 1.

Figure 10A:
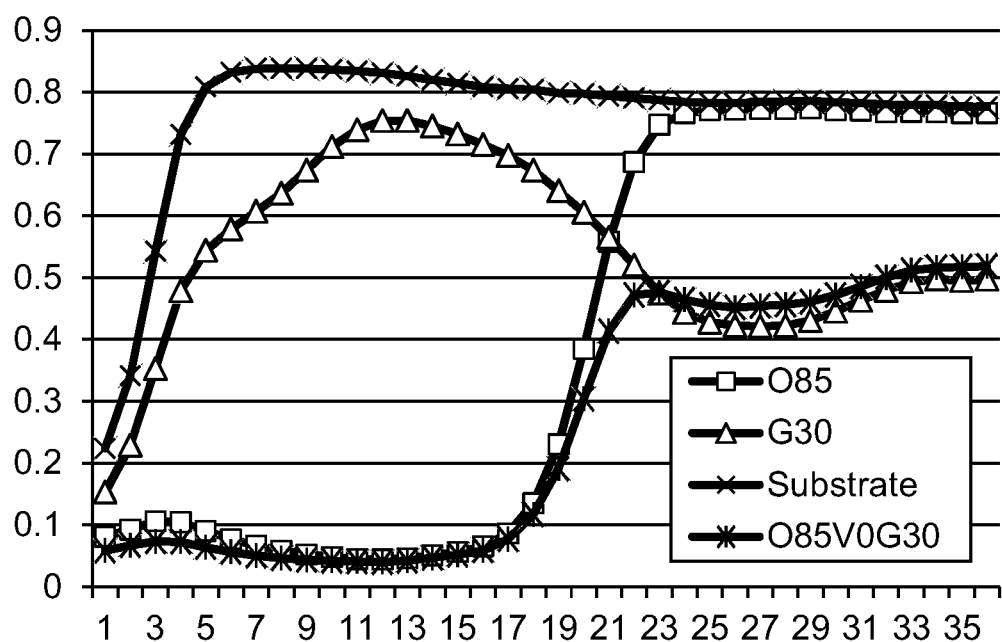
FIG. 10A shows an example of the measured reflectance spectra of the substrate and of O at 85% and G at 30%, as well as the spectral measure of reflectance, calculated in accordance with an embodiment of the invention, of an overprint of 85% O, and 30% G in the printing order orange then green.

FIG. 10A shows another example of the measured spectra of the substrate and of O at an amount 85% and G at 30% for the same gravure system as for FIGS. 9A and 9B on the same substrate, as well as the calculated spectrum of an overprint of 85% O, and 30% G. The actual spectrum of an overprint also was measured, and a measure of the color difference ΔE between the calculated and measured colors was determined to be 1.8.

Figure 10B:
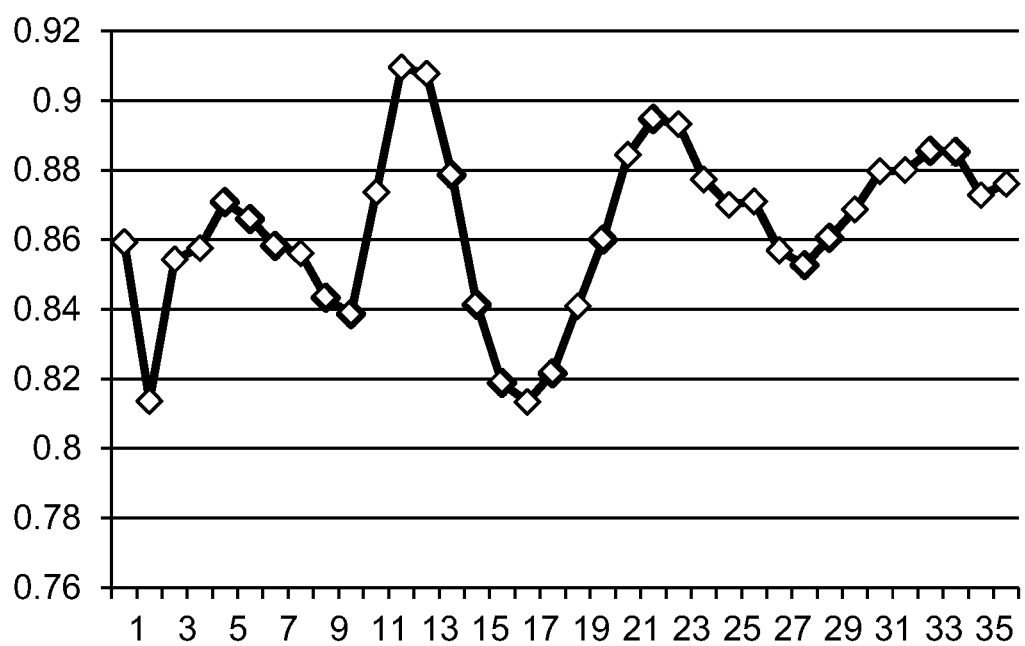
FIG. 10B shows the IAR functions for the green ink at 30% used to determine the overprint spectrum of FIG. 10A in accordance with an embodiment of the present invention.

FIG. 10B shows the IAR function for the green (G) ink at 30%, used to determine the overpring spectrum of FIG. 10A. Note again that the IAR function for the first ink (in this case orange) is always 1.

Thus, methods and a computer readable media with instructions that when executed carry out such methods have been described for determining, e.g., on a processing apparatus the spectral measure of an overprint of a plurality of colors.

Unless specifically stated otherwise, as apparent from the following description, it is appreciated that throughout the specification discussions utilizing terms such as "processing," "computing," "calculating," "determining" or the like, may refer to, without limitation, the action and/or processes of hardware, e.g., an electronic circuit, a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

Note that when a method is described that includes several elements, e.g., several steps, no ordering of such elements, e.g., of such steps is implied, unless specifically stated.

As described above, the methodologies described herein are, in some embodiments, performable by one or more processors that accept logic, instructions encoded on one or more computer-readable media. When executed by one or more of the processors, the instructions cause carrying out at least one of the methods described herein. Any processor capable of executing a set of instructions (sequential or otherwise) that specify actions to be taken is included. Thus, one example is a typical processing system as shown in FIG. 5. The processing system may include one or more of a CPU or similar element, a graphics processing unit (GPU), field-programmable gate array, application-specific integrated circuit, and/or a programmable DSP unit. If manual data entry is required, the processing system also includes an input device such as one or more of an alphanumeric input unit such as a keyboard, a pointing control device such as a mouse, and so forth. The term storage, storage device, storage subsystem, or memory unit as used herein, if clear from the context and unless explicitly stated otherwise, also encompasses a storage system such as a disk drive unit. The processing system in some configurations may include a sound output device, and a network interface device.

In some embodiments, a non-transitory computer-readable medium is configured with, e.g., encoded with instructions, e.g., logic that when executed by one or more processors of a processing system such as a digital signal processing device or subsystem that includes at least one processor element and a storage subsystem, cause carrying out a method as described herein. Some embodiments are in the form of the logic itself. A non-transitory computer-readable medium is any computer-readable medium that is statutory subject matter under the patent laws applicable to this disclosure, including Section 101 of Title 35 of the United States Code. A non-transitory computer-readable medium is for example any computer-readable medium that is not specifically a transitory propagated signal or a transitory carrier wave or some other transitory transmission medium. The term "non-transitory computer-readable medium" thus covers any tangible computer-readable storage medium. In a typical processing system as described above, the storage subsystem thus includes a computer-readable storage medium that is configured with, e.g., encoded with instructions, e.g., logic, e.g., software that when executed by one or more processors, causes carrying out one or more of the method steps described herein. The software may reside in the hard disk, or may also reside, completely or at least partially, within the memory, e.g., RAM and/or within the processor registers during execution thereof by the computer system. Thus, the memory and the processor registers also constitute a non-transitory computer-readable medium on which can be encoded instructions to cause, when executed, carrying out method steps. Non-transitory computer-readable media include any tangible computer-readable storage media and may take many forms including non-volatile storage media and volatile storage media. Non-volatile storage media include, for example, static RAM, optical disks, magnetic disks, and magneto-optical disks. Volatile storage media includes dynamic memory, such as main memory in a processing system, and hardware registers in a processing system.

While the computer-readable medium is shown in an example embodiment to be a single medium, the term "medium" should be taken to include a single medium or multiple media (e.g., several memories, a centralized or distributed database, and/or associated caches and servers) that store the one or more sets of instructions.

Furthermore, a non-transitory computer-readable medium, e.g., a computer-readable storage medium may form a computer program product, or be included in a computer program product.

In alternative embodiments, the one or more processors operate as a standalone device or may be connected, e.g., networked to other processor(s), in a networked deployment, or the one or more processors may operate in the capacity of a server or a client machine in server-client network environment, or as a peer machine in a peer-to-peer or distributed network environment. The term processing system encompasses all such possibilities, unless explicitly excluded herein. The one or more processors may form a personal computer (PC), a print controller, a Web appliance, a network router, switch or bridge, or any machine capable of executing a set of instructions (sequential or otherwise) that specify actions to be taken by that machine.

Note that while some diagram(s) only show(s) a single processor and a single storage subsystem, e.g., a single memory that stores the logic including instructions, those skilled in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Thus, as will be appreciated by those skilled in the art, embodiments of the present invention may be embodied as a method, an apparatus such as a special purpose apparatus, an apparatus such as a data processing system, logic, e.g., embodied in a non-transitory computer-readable medium, or a computer-readable medium that is encoded with instructions, e.g., a computer-readable storage medium configured as a computer program product. The computer-readable medium is configured with a set of instructions that when executed by one or more processors cause carrying out method steps. Accordingly, aspects of the present invention may take the form of a method, an entirely hardware embodiment, an entirely software embodiment or an embodiment combining software and hardware aspects. Furthermore, the present invention may take the form of program logic, e.g., a computer program on a computer-readable storage medium, or the computer-readable storage medium configured with computer-readable program code, e.g., a computer program product.

It will also be understood that embodiments of the present invention are not limited to any particular implementation or programming technique and that the invention may be implemented using any appropriate techniques for implementing the functionality described herein. Furthermore, embodiments are not limited to any particular programming language or operating system.

Reference throughout this specification to "one embodiment," "an embodiment," "some embodiments," or "embodiments" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the DESCRIPTION OF EXAMPLE EMBODIMENTS are hereby expressly incorporated into this DESCRIPTION OF EXAMPLE EMBODIMENTS, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

As used herein, unless otherwise specified, the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

All U.S. patents, U.S. patent applications, and International (PCT) patent applications designating the United States cited herein are hereby incorporated by reference, except in those jurisdictions that do not permit incorporation by reference, in which case the Applicant reserves the right to insert any portion of or all such material into the specification by amendment without such insertion considered new matter. In the case the Patent Rules or Statutes do not permit incorporation by reference of material that itself incorporates information by reference, the incorporation by reference of the material herein excludes any information incorporated by reference in such incorporated by reference material, unless such information is explicitly incorporated herein by reference.

Any discussion of other art in this specification should in no way be considered an admission that such art is widely known, is publicly known, or forms part of the general knowledge in the field at the time of invention.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting of only elements A and B. Any one of the terms including or which includes or that includes as used herein is also an open term that also means including at least the elements/features that follow the term, but not excluding others. Thus, including is synonymous with and means comprising.

Similarly, it is to be noticed that the term coupled, when used in the claims, should not be interpreted as being limitative to direct connections only. The terms "coupled" and "connected," along with their derivatives, may be used. It should be understood that these terms are not intended as synonyms for each other, but may be. Thus, the scope of the expression "a device A coupled to a device B" should not be limited to devices or systems wherein an input or output of device A is directly connected to an output or input of device B. It means that there exists a path between device A and device B which may be a path including other devices or means in between. Furthermore, coupled to does not imply direction. Hence, the expression "a device A is coupled to a device B" may be synonymous with the expression "a device B is coupled to a device A." "Coupled" may mean that two or more elements are either in direct physical or electrical contact, or that two or more elements are not in direct contact with each other but yet still co-operate or interact with each other.

In addition, use of the "a" or "an" are used to describe elements and components of the embodiments herein. This is done merely for convenience and to give a general sense of the invention. This description should be read to include one or at least one and the singular also includes the plural unless it is obvious that it is meant otherwise.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention, to the extent permitted by law. For example, to the extent permitted by law: any formulas given above are merely representative of procedures that may be used; functionality may be added or deleted from the block diagrams and operations may be interchanged among functional blocks; and steps may be added to or deleted from methods described within the scope of the present invention.

We claim:

1. A method of operating a processing apparatus to determine a spectral measure of reflectance of an overprint of a plurality of inks made on a substrate using a printing process, the method comprising:
   (a) accepting in the processing apparatus a spectral measure of reflectance of a substrate at a plurality of wavelengths;
   (b) accepting in the processing apparatus a pre-defined order of printing an overprint of a plurality of inks on the substrate;
   (c) for each ink of the plurality of inks, for a respective amount of printing of the ink, accepting or determining in the processing apparatus a respective interaction of absorption and reflection function ("IAR function") indicative of how the ink interacts with a layer of one or more other inks when printed over the layer of the one or more other inks; and
   (d) determining in the processing apparatus the spectral measure of reflectance of the overprint of the plurality of inks printed on the substrate in the pre-defined order in the respective amounts of the inks, including repeatedly multiplying, in the pre-defined order, for each additional ink added to a partial overprint of the inks before the additional ink is added, the spectral measure of the partial overprint by the exponentiation of:
      (i) the ratio of the spectral measure of the additional ink on the substrate to the spectral measure of the substrate, by (ii) the IAR function of the additional ink, starting with spectral measure of the substrate.

2. A method as recited in claim 1, wherein the determining of the spectral measure is for a plurality of wavelengths.

3. A method as recited in claim 1, wherein the IAR function for a particular amount of a particular ink of the plurality of inks is determined from spectral measures of reflectance of the substrate and of prints made using the printing process of various amounts of the particular ink on the substrate, and one or both of on a gray background and on a black background.

4. A method as recited in claim 3, wherein the gray background comprises black ink printed at 50% coverage amount on the substrate using the printing process.

5. A method as recited in claim 1, wherein the IAR function for a particular amount of a particular ink of the plurality of inks printed over a second ink is determined from spectral measures of reflectance of the substrate and of prints made using the printing process of various coverage percentages of the particular ink and of the second ink on the substrate and overprint charts made using the printing process on the substrate with a set of inks that includes the particular and the second inks.

6. A method as recited in claim 1, wherein the IAR function for a particular amount of a particular ink of the plurality of inks printed over a second ink is determined from spectral measures of reflectance of the substrate and from spectral measures of reflectance of prints made using the printing process of various coverage percentages of the particular ink and of the second ink on the substrate, and from overprint charts made using the printing process on the substrate for process inks.

7. A method as recited in claim 6, wherein the spectral measure of an overprint of the particular ink printed over the second ink is determined by determining the process ink amounts corresponding to the spectral measures of reflectance of the prints made with the particular ink and of prints made using the second ink, determining the process ink amounts of the overprint of the particular ink printed over the second ink, and determining the spectral measure of the overprint of the particular ink printed over the second ink from the determined process ink amounts of the overprint.

8. A method as recited in claim 1, wherein determining the IAR function for a particular ink on a particular background includes using the spectral measure of the substrate, the spectral measure of a first background, the spectral measure of the particular ink on the substrate, and the spectral measure of the particular ink on the first background, and calculating the IAR function of the particular ink on the first background using:

$$IAR(d_a; j) = \frac{\log R(d_g, d_a; j) - \log R(d_g; j)}{\log R(d_a; j) - \log R_0(j)},$$

or an equivalent formula,
where $IAR(d_a; j)$ denotes the IAR function for the particular ink in amount $d_a$ at wavelengths of index j, $R_0(j)$, $R(d_g; j)$, and $R(d_a; j)$ denote the spectral measures of the substrate, the first background in amount $d_g$, and the particular ink at in amount $d_a$, respectively, at wavelengths of index j, $R(d_g, d_a; j)$ denotes the spectral measures of the print of the particular ink on the first background, and log represents the logarithm function in a pre-defined base.

9. A method as recited in claim 8, wherein the IAR function for the particular ink on the particular background is the IAR function determined for the particular ink on the first background.

10. A method as recited in claim 8, wherein the IAR function for the particular ink on the particular background is the IAR function determined for the particular ink on the first background adjusted by exponentiation by an adjustment exponent equal to the ratio of the spectral measures of the particular background to the first background.

11. A method as recited in claim 1, further comprising determining from the spectral measure of reflectance of the overprint a profile for printing an overprint of the inks in the pre-defined order using the printing process.

12. A method of operating a processing apparatus to characterize an ink when the ink is printed over a second ink or over an overprint of one or more other inks on a substrate using a printing process, the method comprising:
   (a) accepting in the processing apparatus a spectral measure of reflectance of the substrate, the spectral measure being at a plurality of wavelengths;

(b) accepting in the processing apparatus the spectral measure of reflectance of the ink printed on the substrate;

(c) accepting in the processing system the spectral measure of reflectance of a first background printed on the substrate;

(d) accepting or determining in the processing system the spectral measure of reflectance of the ink printed on the first background; and (e) determining in the processing system an interaction of absorption and reflection function ("IAR function") for a plurality of wavelengths indicative of how the ink interacts with a background on which it is printed, and usable for determining the spectral measure of an overprint of the ink over a print of one other ink or an overprint of two or more other inks on the substrate by multiplying the spectral measure of reflectance of the print or overprint of one or more other inks by the exponentiation of
  (i) the ratio of the spectral measure of the ink on the substrate to the spectral measure of the substrate, by
  (ii) the TAR function of the ink.

13. A method as recited in claim 12, wherein the first background is one of the set of backgrounds consisting of a gray background on the substrate and a black background on the substrate.

14. A method as recited in claim 13, wherein the gray background comprises black ink printed at 50% coverage amount on the substrate using the printing process.

15. A method as recited in claim 12, wherein determining the TAR function for an amount of the ink over the first background is determined from spectral measures of reflectance of the substrate and of prints made using the printing process of various coverage percentages of the ink and of the first background on the substrate and overprint charts made using the printing process for process inks.

16. A method as recited in claim 15, wherein the spectral measure of an overprint of the particular ink printed over first background is determined by determining the process ink amounts corresponding to the spectral measures of reflectance of the prints made with the particular ink and of the first background, determining the process ink amounts of the overprint of the particular ink printed over the first background, and determining the spectral measure of the overprint of the particular ink printed over first background from the determined process ink amounts of the overprint.

17. A method as recited in claim 12, wherein determining the IAR function for the ink on the first background includes using the spectral measure of the substrate, the spectral measure of a particular background, the spectral measure of the ink on the substrate, and the spectral measure of the ink on the particular background, and calculating the IAR function of the ink on the particular background using:

$$IAR(d_a; j) = \frac{\log R(d_g, d_a; j) - \log R(d_g; j)}{\log R(d_a; j) - \log R_0(j)},$$

or an equivalent formula,
where $IAR(d_a; j)$ denotes the IAR function for the ink in amount $d_a$ at wavelengths of index j, $R_0(j)$, $R(d_g; j)$, and $R(d_a; j)$ denote the spectral measures of the substrate, the particular background in amount $d_g$, and the ink at in amount $d_a$, respectively, at wavelengths of index j, $R(d_g, d_a; j)$ denotes the spectral measures of the print of the ink on the particular background, and log represents the logarithm function in a pre-defined base.

18. A method as recited in claim 17, wherein the IAR function for the ink on the first background is the IAR function determined for the ink on the particular background.

19. A method as recited in claim 17, wherein the IAR function for the ink on the first background is the IAR function determined for the ink on the particular background adjusted by exponentiation by an adjustment exponent equal to the ratio of the spectral measures of the first background to the particular background.

20. A method as recited in claim 12, wherein the IAR function includes a piecewise linear function of wavelength determined by values of the IAR function at a number of wavelengths.

21. A non-transitory computer-readable medium with a set of instructions thereon that when executed by one or more processors of a processing system cause carrying out a method of determining a spectral measure of reflectance of an overprint of a plurality of inks made on a substrate using a printing process, the method comprising:

(a) accepting in the processing system a spectral measure of reflectance of a substrate at a plurality of wavelengths;

(b) accepting in the processing system a pre-defined order of printing an overprint of a plurality of inks on the substrate;

(c) for each ink of the plurality of inks, for a respective amount of printing of the ink, accepting or determining in the processing system a respective interaction of absorption and reflection function ("IAR function") indicative of how the ink interacts with a layer of one or more other inks when printed over the layer of the one or more other inks; and (d) determining in the processing system the spectral measure of reflectance of the overprint of the plurality of inks printed on the substrate in the pre-defined order in the respective amounts of the inks, including repeatedly multiplying, in the pre-defined order, for each additional ink added to a partial overprint of the inks before the additional ink is added, the spectral measure of the partial overprint by the exponentiation of:
  (i) the ratio of the spectral measure of the additional ink on the substrate to the spectral measure of the substrate
  by
  (ii) the TAR function of the additional ink,
starting with spectral measure of the substrate.

22. An apparatus to determine a spectral measure of reflectance of an overprint of a plurality of inks made on a substrate using a printing process, the apparatus comprising:
  one or more processors; and
  storage,
wherein the storage comprising instructions that when carried out by one or more of the apparatus to:

(a) accept in the apparatus a spectral measure of reflectance of a substrate at a plurality of wavelengths;

(b) accept a pre-defined order of printing an overprint of a plurality of inks on the substrate;

(c) for each ink of the plurality of inks, for a respective amount of printing of the ink, accept or determine a respective interaction of absorption and reflection function ("IAR function") indicative of how the ink interacts with a layer of one or more other inks when printed over the layer of the one or more other inks; and (d) determine the spectral measure of reflectance of the overprint of the plurality of inks printed on the substrate in the pre-defined order in the respective amounts of the inks, including repeatedly multiplying, in the pre-defined order, for each additional ink added to a partial overprint of the inks before the additional ink is added, the spectral measure of the partial overprint by the exponentiation of:
(i) the ratio of the spectral measure of the additional ink on the substrate to the spectral measure of the substrate,
by
(ii) the TAR function of the additional ink,
starting with spectral measure of the substrate.

* * * * *

UNITED STATES PATENT AND TRADEMARK OFFICE
CERTIFICATE OF CORRECTION

PATENT NO. : 9,347,874 B2
APPLICATION NO. : 13/870940
DATED : May 24, 2016
INVENTOR(S) : Keydar et al.

Page 1 of 3

It is certified that error appears in the above-identified patent and that said Letters Patent is hereby corrected as shown below:

In the specification

In column 2, line 20, change "0" to --O--

In column 2, line 23, change "0" to --O--

In column 2, line 33, change "0" to --O--

In column 5, line 26, change "CIEXYZ" to --CIE-XYZ--

In column 6, line 63, change "$P_1 \leftarrow P \leftarrow ... \leftarrow P_n$" to --$P_1 \leftarrow P_2 \leftarrow ... \leftarrow P_n$--

In column 7, line 34, change the equation

" $R(d_1, d_2, ..., d_n, j) = R_0(j) \times W(d_1, j)^{IAR(d_1, d)}$ "

to

-- $R(d_1, d_2, ..., d_n, j) = R_0(j) \times W(d_1, j)^{IAR(d_1, j)}$ --

In column 7, line 42, change "Pi" to --$P_i$--

In column 8, line 38, change "technology-Input" to --technology --Input--

In column 10, line 20, change the equation

" $IAR(d_a;j)|_c = (IAR(d_a;j)|_g) R(d_c;j) / R(d_g;j)$ "

to

-- $IAR(d_a;j)|_c = (IAR(d_a;j)|_g)^{R(d_c;j)/R(d_g;j)}$ --

Signed and Sealed this
Sixteenth Day of August, 2016

Michelle K. Lee
*Director of the United States Patent and Trademark Office*

CERTIFICATE OF CORRECTION (continued)
U.S. Pat. No. 9,347,874 B2

In column 10, line 55, change the equation

" $IAR(d_a;j)|_c = (IAR(d_a;j)|_b) R(d_c;j)/R(d_b;j)$ ,"

to

-- $IAR(d_a;j)|_c = (IAR(d_a;j)|_b)^{R(d_c;j)/R(d_b;j)}$ --

In column 11, line 3, change "CIEXYZ" to --CIE-XYZ--

In column 11, line 33, change "CIEXYZ" to --CIE-XYZ--

In column 11, line 36, change "CIEXYZ" to --CIE-XYZ--

In column 11, line 44, change "CIEXYZ" to --CIE-XYZ--

In column 11, line 47, change "CIEXYZ" to --CIE-XYZ--

In column 12, line 9, change "CIEXYZ" to --CIE-XYZ--

In column 12, line 24, change the equation

" $\Delta E_{XYZ}^2 = (X_{current} - X_{previous})^2 + (Y_{current} - Y_{previous})^2 + (Z_{current} - Z_{previous})^2$ ,"

to

-- $\Delta E_{XYZ}^2 = (X_{current} - X_{previous})^2 + (Y_{current} - Y_{previous})^2 + (Z_{current} - Z_{previous})^2$ --

In column 12, line 27, change " $\Delta E_{XYZ}^2 < \Delta e_T^2$, where $\Delta e_T^2$ " to -- $\Delta E_{XYZ}^2 < \Delta e_T^2$, where $\Delta e_T^2$ --

In column 12, line 28, change " $\Delta E_{XYZ}^2$ " to -- $\Delta E_{XYZ}^2$ --

In column 12, line 44, change " $\Delta E_{XYZ}$ or $\Delta E_{XYZ}^2$ " to -- $\Delta E_{XYZ}$ or $\Delta E_{XYZ}^2$ --

In column 13, lines 25–26, change "x(j)=j/L-1" to --x(j)=j/(L-1)--

In column 13, line 27, change "$x_m$= 0.0" to --$x_{min}$= 0.0--

In column 13, line 39, change "(j=l–1; x=$x_{max}$)" to --(j=L–1; x=$x_{max}$)--

In column 15, line 18, change "overpring" to --overprint--

CERTIFICATE OF CORRECTION (continued)
U.S. Pat. No. 9,347,874 B2

In the claims

In column 21, line 30 (claim 15, line 2), change "TAR" to --IAR--

In column 22, line 44 (claim 21, line 30), change "TAR" to --IAR--

In column 23, line 6 (claim 22, line 28), change "TAR" to --IAR--